(12) United States Patent
Wieland

(10) Patent No.: US 10,258,381 B2
(45) Date of Patent: Apr. 16, 2019

(54) CONICAL END CAP FOR INTRAMEDULLARY NAIL

(71) Applicant: Stryker European Holdings I, LLC, Kalamazoo, MI (US)

(72) Inventor: Manfred Wieland, Kiel (DE)

(73) Assignee: Stryker European Holdings I, LLC, Kalamazoo, MI (US)

(*) Notice: Subject to any disclaimer, the term of this patent is extended or adjusted under 35 U.S.C. 154(b) by 151 days.

(21) Appl. No.: 15/323,262

(22) PCT Filed: Jul. 3, 2014

(86) PCT No.: PCT/EP2014/064232
§ 371 (c)(1),
(2) Date: Dec. 30, 2016

(87) PCT Pub. No.: WO2016/000784
PCT Pub. Date: Jan. 7, 2016

(65) Prior Publication Data
US 2017/0360479 A1 Dec. 21, 2017

(51) Int. Cl.
| A61B 17/72 | (2006.01) |
| A61B 17/86 | (2006.01) |
| A61B 17/84 | (2006.01) |
| A61B 17/68 | (2006.01) |

(52) U.S. Cl.
CPC ......... *A61B 17/685* (2013.01); *A61B 17/72* (2013.01); *A61B 17/7283* (2013.01); *A61B 17/846* (2013.01); *A61B 17/86* (2013.01); *A61B 17/8625* (2013.01)

(58) Field of Classification Search
CPC .................. A61B 17/685; A61B 17/72
See application file for complete search history.

(56) References Cited

U.S. PATENT DOCUMENTS

| 3,133,578 A * | 5/1964 | Moskovitz | F16B 39/30 |
| | | | 411/309 |
| 3,364,807 A * | 1/1968 | Holton | B21K 1/64 |
| | | | 411/436 |
| 4,167,355 A * | 9/1979 | Hansson | F16B 2/065 |
| | | | 403/374.3 |

(Continued)

FOREIGN PATENT DOCUMENTS

| CN | 102188282 A | 9/2011 |
| DE | 20316200 U1 | 12/2003 |

(Continued)

OTHER PUBLICATIONS

PCT/EP2015/065251 International Search Report dated Sep. 18, 2015, 4 pages.

(Continued)

*Primary Examiner* — Christian Sevilla
(74) *Attorney, Agent, or Firm* — Lerner, David, Littenberg, Krumholz & Mentlik, LLP

(57) ABSTRACT

An end cap is provided comprising a head with a tool engagement portion and a shaft with a tip, wherein the shaft comprises a threaded conical portion starting from the tip and extending in a direction to the head. The thread may be provided with a constant pitch, i.e. with a constant distance between the turns of the thread.

19 Claims, 6 Drawing Sheets

(56) References Cited

U.S. PATENT DOCUMENTS

| | | | | |
|---|---|---|---|---|
| 4,917,555 | A * | 4/1990 | Taubert | F16B 5/0275 411/168 |
| 5,340,254 | A * | 8/1994 | Hertel | F16B 25/0021 411/311 |
| 5,827,030 | A * | 10/1998 | Dicke | F16B 25/0015 411/387.4 |
| 6,152,666 | A * | 11/2000 | Walther | F16B 25/0015 411/311 |
| 6,450,748 | B1 * | 9/2002 | Hsu | F16B 25/0015 411/387.4 |
| 6,508,820 | B2 * | 1/2003 | Bales | A61B 17/725 606/104 |
| 6,527,775 | B1 * | 3/2003 | Warburton | A61B 17/164 606/62 |
| 7,021,877 | B2 * | 4/2006 | Birkelbach | F16B 25/0021 411/412 |
| 9,173,042 | B2 * | 10/2015 | Jinton | A61C 8/0025 |
| 2001/0014262 | A1 * | 8/2001 | Friederich | C21D 6/02 411/386 |
| 2007/0269288 | A1 * | 11/2007 | Palm | F16B 25/0021 411/386 |
| 2012/0330313 | A1 * | 12/2012 | Grady | A61B 17/7225 606/64 |

FOREIGN PATENT DOCUMENTS

| | | |
|---|---|---|
| DE | 102004034246 A1 | 2/2006 |
| EP | 2364657 A1 | 9/2011 |
| WO | 2014015942 A1 | 1/2014 |

OTHER PUBLICATIONS

PCT/EP2014/064232 International Search Report dated Mar. 5, 2015, 3 pages.

* cited by examiner

Detail A

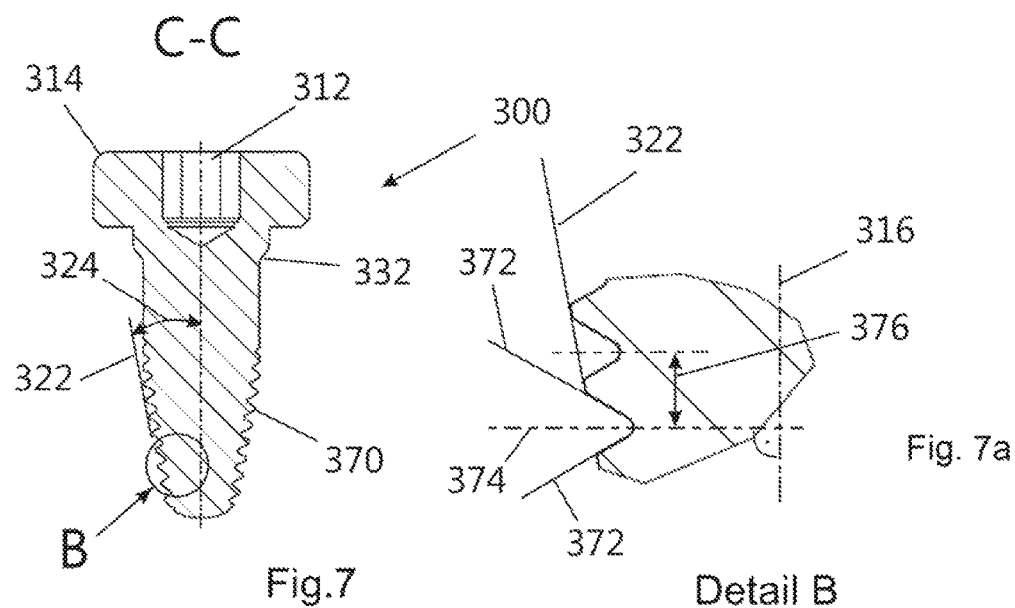
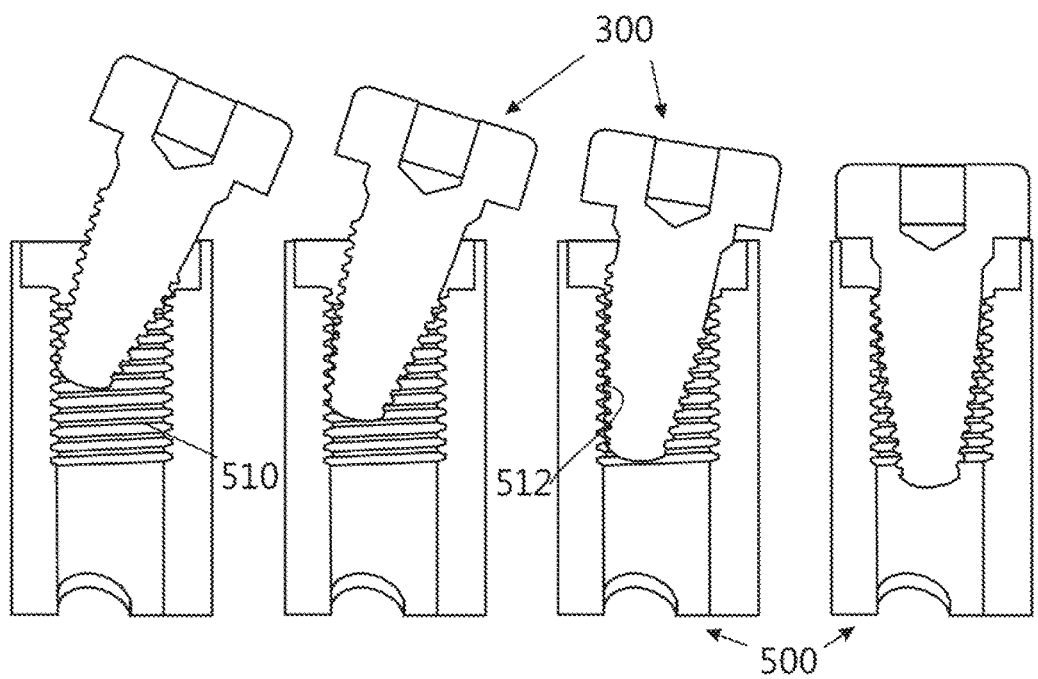

CONICAL END CAP FOR INTRAMEDULLARY NAIL

CROSS-REFERENCE TO RELATED APPLICATIONS

The present application is a national phase entry under 35 U.S.C. § 371 of International Application No. PCT/EP2014/064232 filed Jul. 3, 2014, published in English as WO 2016/000784 A1, which is incorporated herein by reference.

FIELD OF THE DISCLOSURE

The invention relates to an implant. In particular, the invention relates to an end cap for use with an intramedullary nail.

BACKGROUND INFORMATION

An implant and particularly a bone implant include a portion or section or end which is adapted to be firstly introduced into a body during an implantation. Such a portion or section or end is usually referred to as leading portion or leading section or leading end. Consequently, an opposite portion or section or end of the implant is adapted to be finally introduced, wherein this portion or section or end may additionally be configured for an engagement of a tool for inserting the implant into the body. Such a portion or section or end is usually referred to as trailing portion or trailing section or trailing end.

A bone implant may be a pin or a nail or screw. A bone nail may be an intramedullary nail, for example a femur nail, a humerus nail or a tibia nail. A bone screw may be a screw for fixing fragments of a bone fracture or may be a locking screw for locking a bone nail in the bone.

However, due to the anatomical variation of bones it may happen that the trailing end of a bone implant sticks out of a bone after implant placement. The trailing end of the implant may act as an interface towards a target or aiming device. In order to create a solid fixation nails may be provided with grooves in order to fit pegs on the post of the target device for accurate alignment, for sufficient fixation, and for controlling the forces applied during implant insertion and removal.

It may occur that patients complain about pain after surgery in this area, especially when the implant is sticking out of the bone. This pain may be caused by sharp edges at the trailing end of the implant. Such edges may cause irritations and/or injuries of the surrounding soft tissue.

On the other hand, the trailing end of a bone nail may be arranged within a bone, i.e. under a bone surface, after an implantation. In such case, bone tissue may grow over the trailing edges of the bone nail resulting in difficulties to explant the bone nail after healing of a treated bone fracture.

To reduce these problems, an end cap in form of a small screw may be inserted into the trailing end of the implant, with the screw having a screw head with a length and smooth and rounded edges.

However, it may be difficult to align the screw axis to an axis of an inner thread in the trailing end of the implant when introducing such a small screw into an implant which is already inserted into a bone and an axis of which is thus not clearly recognizable, i.e. visible, as can be seen in FIG. 9. Consequently, a small screw as an end cap may easily tilt during insertion.

SUMMARY OF THE INVENTION

An object may be defined as providing an end cap for an implant, wherein an introduction of the end cap into a trailing end of an implant is facilitated.

This is achieved by the end cap according to the independent claim. Further embodiments are described in the dependent claims.

In general, an end cap comprises a head with a tool engagement portion and a shaft with a tip, wherein the shaft comprises a threaded conical portion starting from the tip and extending in a direction to the head. The thread may be provided with a constant pitch, i.e. with a constant distance between the turns of the thread. In other words, the distance between each of two adjacent turns of the thread is the same, when measured in a longitudinal direction of the end cap.

According to an embodiment, the thread at the shaft of the end cap may comprise a thread profile defining a centre axis between two adjacent tooth flanks, wherein the centre axis of the thread profile is perpendicular to the surface of the conical portion. Alternatively, the centre axis of the thread profile may be perpendicular to the longitudinal axis of the conical portion. It will be understood that the centre axis of the thread profile may also be in the middle or at any other angle between the mentioned alternative centre axes.

According to an embodiment, the conical portion of the shaft of the end cap defines an angle of between 8° and 12° to a longitudinal axis of the end cap. For example, the conical portion may define an angle of 10° to the longitudinal axis.

In general, a thread may be described by a major diameter and a minor diameter. The major diameter of a thread is the larger of two extreme diameters delimiting the height of the thread profile, as a cross-sectional view is taken in a plane containing the axis of the threads. The minor diameter is the lower extreme diameter of the thread. Major diameter minus minor diameter, divided by two, equals the height of the thread. It will be understood that a nominal diameter of an outer thread will actually differ from the major diameter of the thread to provide a clearance between the outer thread and a corresponding inner thread. Without such a clearance, the threads would not be able to move relative to each other.

According to an embodiment, the thread at the shaft of the end cap may have a maximal outer diameter, i.e. a maximal major diameter adjacent to the head, which diameter corresponds to a nominal diameter of an inner thread of an implant. For example, the maximal major diameter of the thread may be 8 mm. A screw with an outer diameter of 8 mm should fit into an inner thread with a nominal diameter of 8 mm, i.e. with a maximal inner diameter of the inner thread of slightly more than 8 mm, i.e. of for example 8.1 mm. It is noted that the thread at the conical portion may have at least one turn adjacent the head of the end cap with the maximal outer diameter.

According to an embodiment, the shaft may further comprise a cylindrical portion starting from the conical portion and extending in a direction to the head, wherein the thread continues with a constant diameter on the cylindrical portion. That is, the thread according to this embodiment may have more than one turn of the thread with the maximal outer diameter.

According to an embodiment, the threaded portion of the shaft may comprise a sub-portion with a first circumferential section without threads and a second circumferential section with threads. The first circumferential section may have an outer diameter corresponding to a minor diameter of the thread. The first circumferential section may extend on at least a third of the circumference of the sub-portion. A smooth transition may be provided in a circumferential direction between the first and second circumferential sections.

According to an embodiment, the thread may have a minimal diameter adjacent to the tip, which minimal diameter may for example be half of the maximal diameter. The tip may have rounded edges. The tip may have a part-spherical shape. Further, the tip may have a blunt end with rounded edges as smooth transition to the first turn of the thread.

According to an embodiment, a clearance groove may be provided on the shaft adjacent the head of the end cap, i.e. between the thread and the head. In the clearance groove, a chamfer may be provided as a transition between the root of the clearance groove and a radially outwardly extending surface of the head.

According to an embodiment, a system may be provided comprising an end cap as described above and a bone nail as well as an aiming or targeting device for assisting an introduction of a locking screw and/or a driving tool for manipulating the bone nail during an implantation of the same.

An exemplary bone nail may be an intramedullary nail comprising a through bore for receiving a locking screw, the through bore extending through the shaft of the bone nail in a direction transverse and possibly also inclined relative to a longitudinal axis of the shaft. The intramedullary nail may further comprise a bore formed at least in the trailing end section of the nail, with the bore extending in a longitudinal direction of the shaft of the nail, the longitudinal bore including an inner thread for releasably fixing a medical device like a driving tool for manipulating the implant during an implantation or like a targeting device, wherein the inner thread is also adapted to receive an end cap in accordance with the invention.

When used with an intramedullary nail, the end cap may further be configured to be a fixation means for a locking screw. The tip of the end cap may be in contact with an outer surface of the shaft of the locking screw within a bone nail, when being inserted into a trailing end of a bone nail. Thus, the end cap allows reducing any pain which may be caused by sharp edges at the trailing end of the implant and preventing any movement of a locking screw relative to the bone nail.

It has to be noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

FIG. 7 is a section view of the end cap of FIGS. 6a, 6b including a detailed view of the thread.

FIG. 7a is an enlarged view of detail B of FIG. 7.

FIGS. 8a-8d show a sequence illustrating an introduction of an end cap of FIGS. 6a, 6b, 7 into a trailing end of a bone nail.

Figure 1:
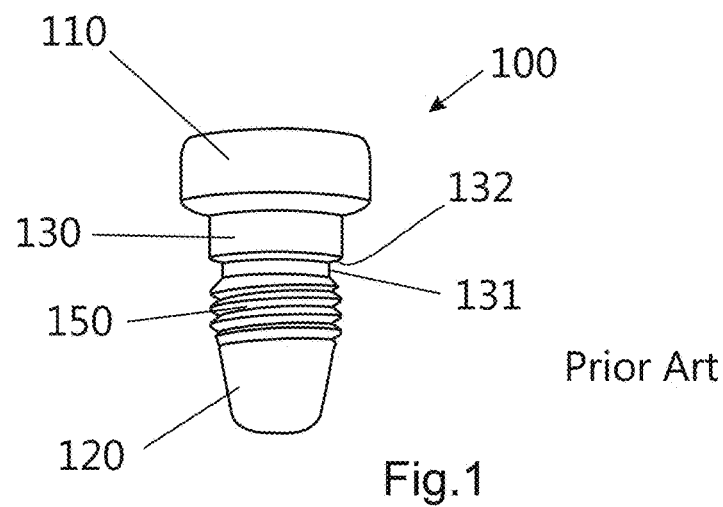
FIG. 1 shows an end cap according to the prior art.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures, as defined by the appended claims.

DETAILED DESCRIPTION OF EXEMPLARY EMBODIMENTS

FIG. 1 shows an end cap in accordance with the prior art. The end cap 100 comprises a head 110, a conical tip portion, a cylindrical portion 150 with an outer thread and an intermediate portion 130. A clearance groove 131 is provided between the thread portion 150 and intermediate portion 130 forming a shoulder 132. The conical tip portion 120 is formed with a smooth outer surface and a rounded tip.

Figures 2A, 2B, 2C, 2D:
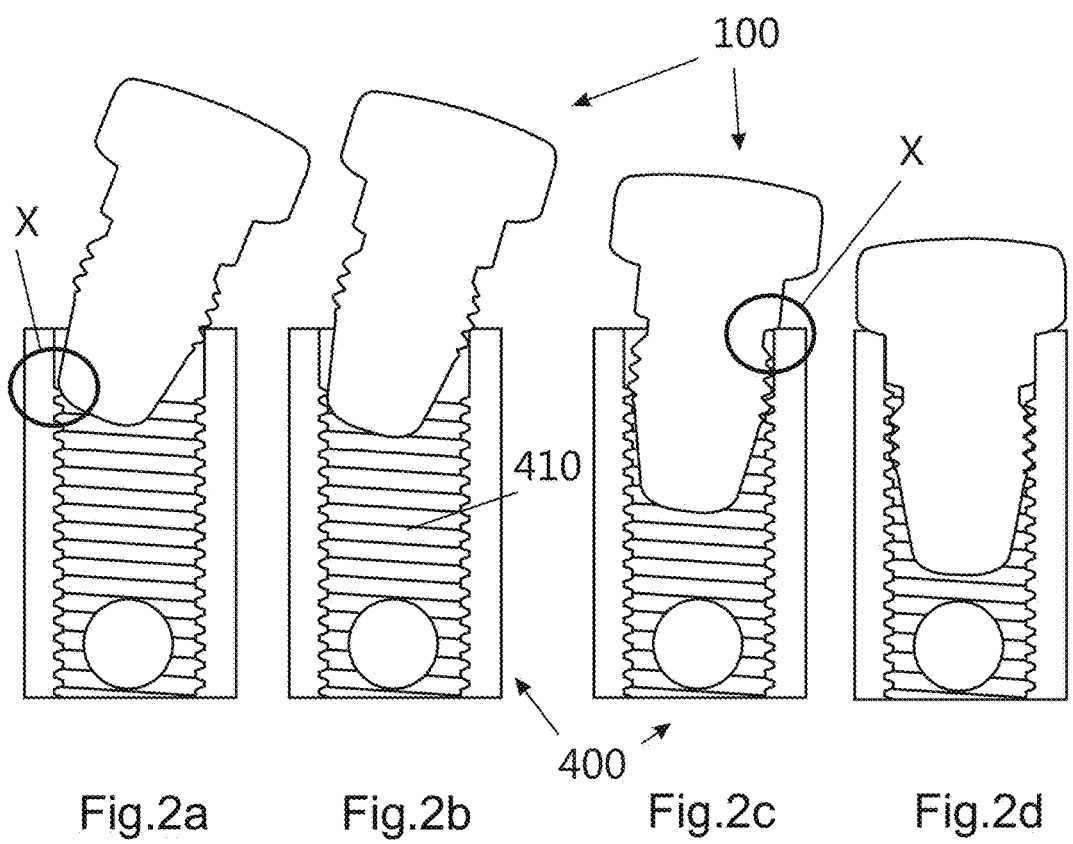
FIGS. 2a-2d show a sequence illustrating an introduction of the prior art end cap of FIG. 1 into a threaded trailing end of a bone nail.

In the sequence of FIGS. 2a-2d, an introduction of an end cap of FIG. 1 is illustrated. In FIG. 2a, the end cap 100 is tilted relative to the axis of the inner thread 410 in the bone nail 400. Such an angled introduction may particularly occur as the introduction of the end cap is performed more or less blindly, keeping in mind that the bone nail is already introduced into a bone (not shown) and the actual orientation of the axis of the bone nail is not recognizable. As indicated with the circle denoted with X, the front end 120 of the end cap will abut the first turn of the inner thread 410, impeding the introduction of end cap 100.

Before the outer threads of the end cap engage with the inner threads 410 of the bone nail 400, shoulder 132 at the intermediate section created by the clearance groove may further hinder an introduction of the end cap 100, as indicated by the circle denoted with X in FIG. 2c.

Figure 3A:
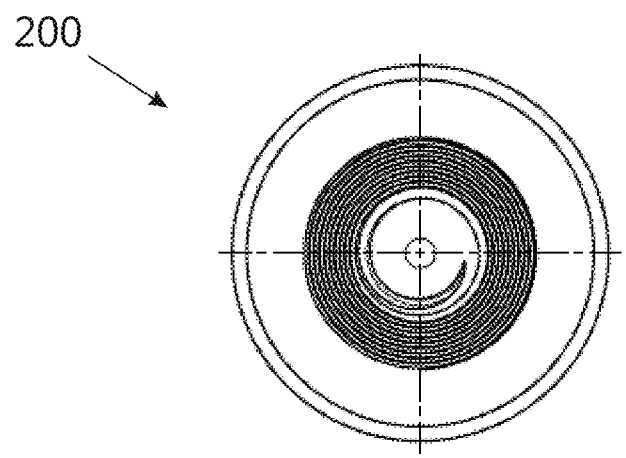
FIGS. 3a and 3b show an end cap according to a first embodiment.
Figure 3B:
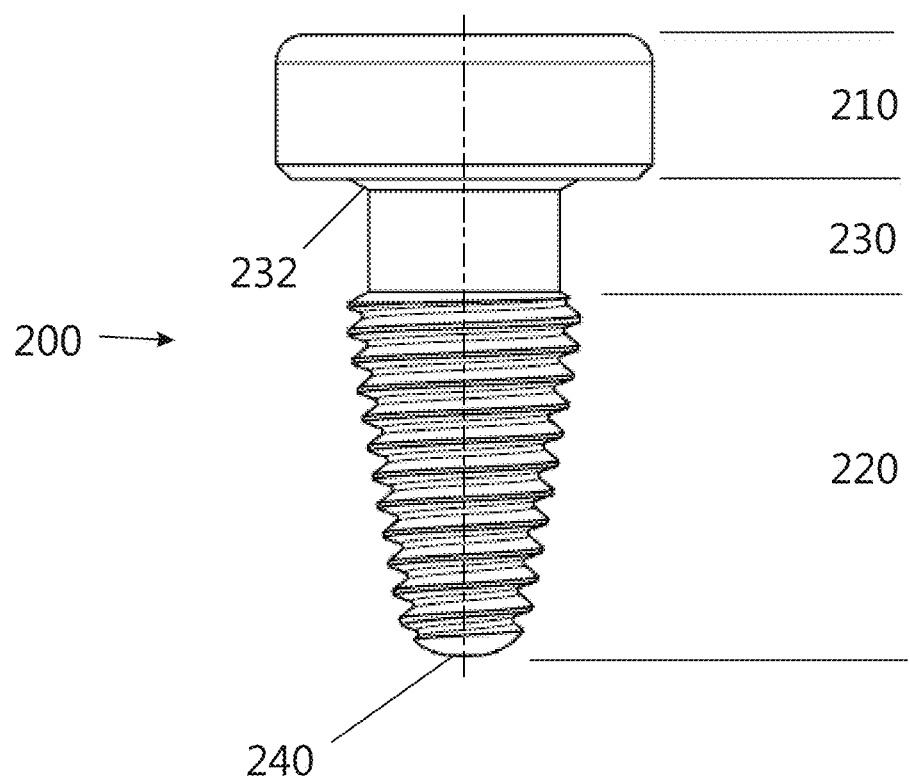

In FIGS. 3a and 3b, an end cap 200 according to a first embodiment is shown, with FIG. 3a being a view onto the tip 240 of the end cap 200, i.e. with a viewing direction from the bottom to the top of FIG. 3b.

The end cap 200 comprises a head 210, a conical portion 220, a clearance groove 230 as well as a tip 240. In this embodiment, the conical portion 220 is completely formed with a thread at the outer surface thereof. As a transition between the clearance groove 230 and the head 210, a chamfer 232 is provided.

Figure 4:
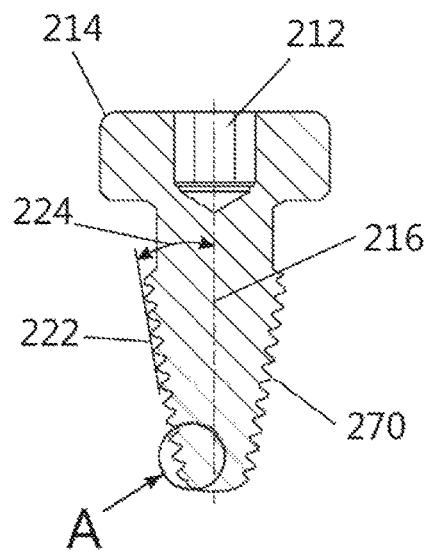
FIG. 4 is a section view of the end cap of FIGS. 3a, 3b including a detailed view of the thread.
Figure 4A:
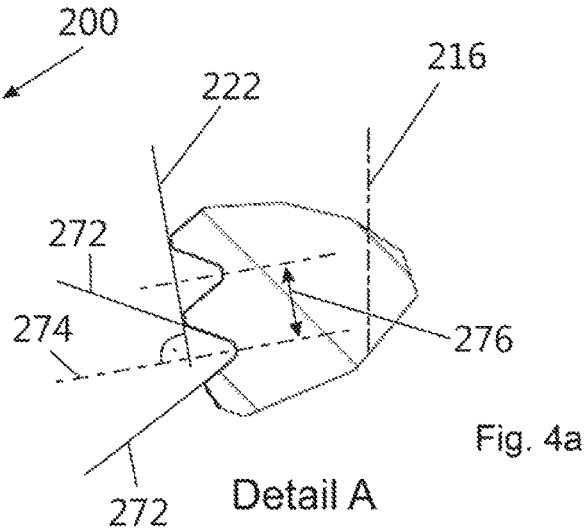
FIG. 4a is an enlarged view of detail A of FIG. 4.

As shown in FIG. 4, the head portion 210 of the end cap 200 comprises an inner tool engagement portion 212 as well as rounded edges 214. The conical portion may be described by an outer surface 222 which is inclined by an angle 224 relative to a longitudinally extending central axis 216 of the end cap 200. Threads 270 are cut into the outer surface 222.

Detail A is an enlarged view of the threads 270. In this embodiment, the threads are cut into the outer surface 222 of the conical portion so as to form two flanks 272. Between the flanks 272, a bisecting line 274 can be defined which is orientated perpendicularly to the outer surface 222. The threads 270 comprise a pitch 276, i.e. a distance between two turns of the threads, which is constant over the length of the threads.

Figures 5A, 5B, 5C, 5D:
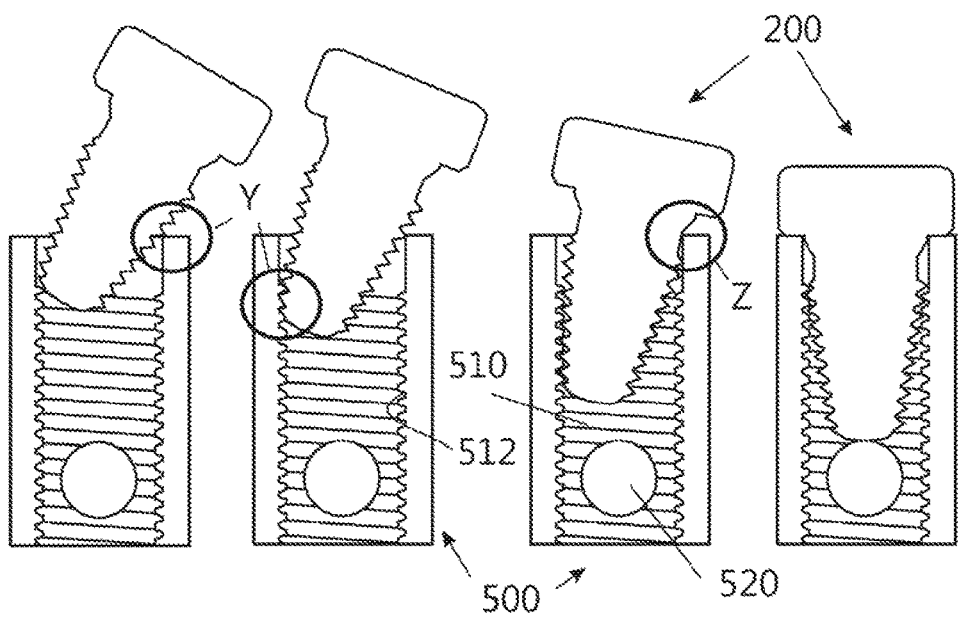
FIGS. 5a-5d show a sequence illustrating an introduction of an end cap of FIGS. 3a, 3b, 4 into a trailing end of a bone nail.

An introduction of an end cap 200 into a trailing end of a bone nail 500 is illustrated by the sequence shown in FIGS. 5a-5d. Assuming that the end cap 200 will be initially inserted into the trailing end of the bone nail 500 in a tilted direction or orientation, as shown in FIG. 5a, the threads on the conical portion of the end cap 200 will engage an edge at the trailing end of the bone nail 500 and/or the first turns of the threads 510 within a bore 512 in the bone nail 500, as indicated by the circle denoted with Y. The conical thread 270 allows screwing in the end cap 200 into the inner threads 510, although the axis 216 of the end cap 200 is inclined relative to the central axis of the bore 512 of bone nail 500, as shown in FIG. 5c. The axis 216 of the end cap 200 will be aligned automatically with the axis of bore 512 of the bone nail 500 by the chamfer 232 provided beneath the head 210 of the end cap, as indicated by the circle denoted with Z in FIG. 5c. Finally, the axis 216 of the end cap will be aligned with the axis of the bore 512 and at least the turn of the outer thread with the maximum diameter will engage the inner threads 510 in the bone nail trailing end.

As shown in FIG. 5d, the end cap 200 may have a length along axis 216 which corresponds to the distance between the trailing end and a first transverse through bore 520 in the bone nail 500. Therefore, the end cap 200 may be configured to be in contact with an outer surface of a locking screw (not shown), when the locking screw is inserted through the through bore 520 and the end cap is completely introduced into the trailing end of the bone nail 500, thus fixing the locking screw within the through bore.

Figure 6A:
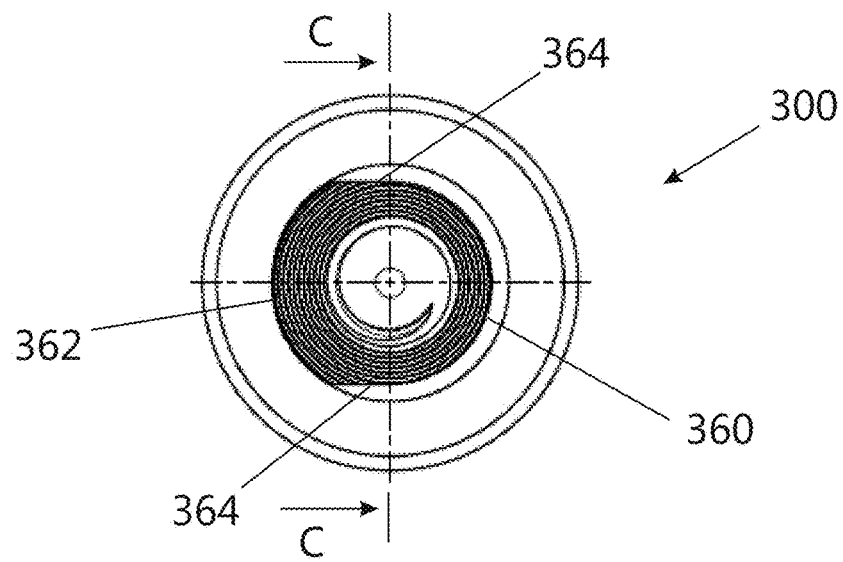
FIGS. 6a and 6b show an end cap according to a second embodiment.
Figure 6B:
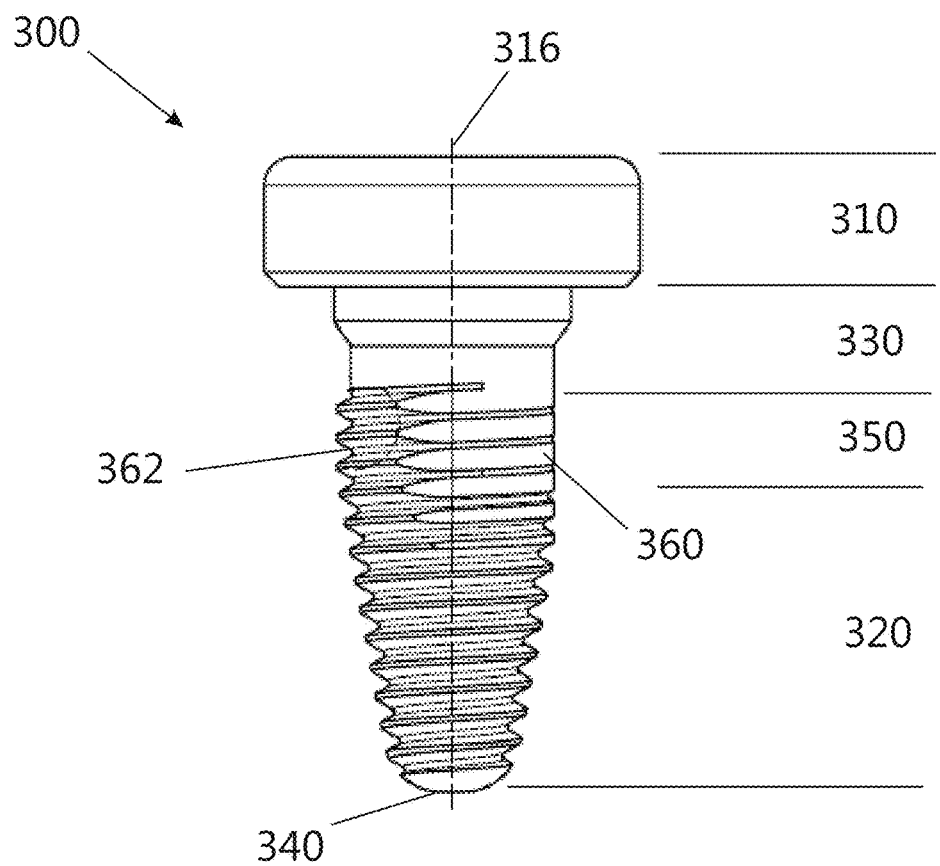

In FIGS. 6a and 6b, an end cap 300 according to a second embodiment is shown, with FIG. 6a being a view onto the tip 340 of the end cap 300.

The end cap 300 comprises a head 310, a conical portion 320, a clearance groove 330 as well as a tip 340, with the conical portion 320 being completely formed with a thread at the outer surface thereof. The end cap 300 further comprises a sub-portion 350. The threads on the conical portion 320 continue over the sub-portion 350, wherein the sub-portion 350 is cylindrically formed, thus having threads with a constant diameter. Furthermore, the sub-portion includes a first circumferential section 360 without threads and a second circumferential section 362 with threads.

As shown in FIG. 7 which is a section view along the section plane C-C as indicated in FIG. 6a, the head portion 310 of the end cap 300 comprises an inner tool engagement portion 312 as well as rounded edges 314. The conical portion may be described by an outer surface 322 which is inclined by an angle 324 relative to a longitudinally extending central axis 316 of the end cap 300.

Threads 370 of the end cap 300 may be generated by firstly cutting threads continuously into the outer surface of the conical portion 320 and into the outer surface of the sub-portion 350, and then removing the threads in the first circumferential section 360 by reducing the outer diameter in this section.

For example, the circumferential section 360 may form 50% of the circumference of the shaft portion and 80% to 100% of the threads may be removed in this section by machining, like for example by grinding or milling. When machining the threads, the shaft may be moved linearly from a side to a machining tool, may then be rotated for 180° about its axis, and may then be moved linearly again and sidewardly away from the machining tool. By way of such process, a circumferential section 360 with two opposite transition sections 364 may be formed, as shown in FIG. 6a, with the transition sections 364 forming a smooth transition from the first circumferential section 360 without threads to the second circumferential section 362 with threads.

Detail B is an enlarged view of the threads 370. In this embodiment, the threads are cut into the outer surface 322 of the conical portion so as to form two flanks 372, between which a bisecting line 374 can be defined which is orientated perpendicularly to the axis 316 of the end cap 300. The threads 370 comprise a pitch 376 which is constant over the length of the threads.

An introduction of an end cap 300 into a trailing end of a bone nail 500 is illustrated by the sequence shown in FIGS. 8a-8d. Also here, assuming that the end cap 300 will be initially inserted into the trailing end of the bone nail 500 in a tilted orientation, as shown in FIG. 8a, the threads 370 on the conical portion of the end cap 300 will engage at least an edge at the trailing end of the bone nail 500 and/or the first turns of the threads 510 within the bore 512 of bone nail 500. The conical thread 370 allows screwing in the end cap 300 into the inner threads 510, although the axis 316 of the end cap 300 is inclined relative to the axis of the bone nail 500, as shown in FIGS. 8b and 8c. The axis of the end cap 300 will be aligned automatically with the central axis of the bore 512 of the bone nail 500 when screwing in the end cap.

As soon as the end cap 300 is completely introduced into the bone nail 500, the turns of the outer thread at the second circumferential section 362 of the sub-portion 350 will engage the inner threads 510 in the bone nail and the axis 316 of the end cap will finally be aligned with the central axis of bore 512 of the bone nail.

As long as the end cap axis 316 is not aligned with the axis of the bone nail, while screwing in the end cap 300, the first circumferential section 360 without threads will prevent any clamping of the threads. With regard to end cap 200 or 300, the diameter of the threads 270, 370 at the conical portion of the end cap 200, 300 is smaller than the diameter of the inner threads 510 in the bone nail 500, and with regard to end cap 300, the thread 370 is provided in a cylindrical portion of the shaft only on one side, so as to avoid an asynchronic engagement of threads on opposite sides, i.e. to avoid for example an engagement of one turn of the outer thread into two different turns of the inner thread on opposite sides.

Figure 9:
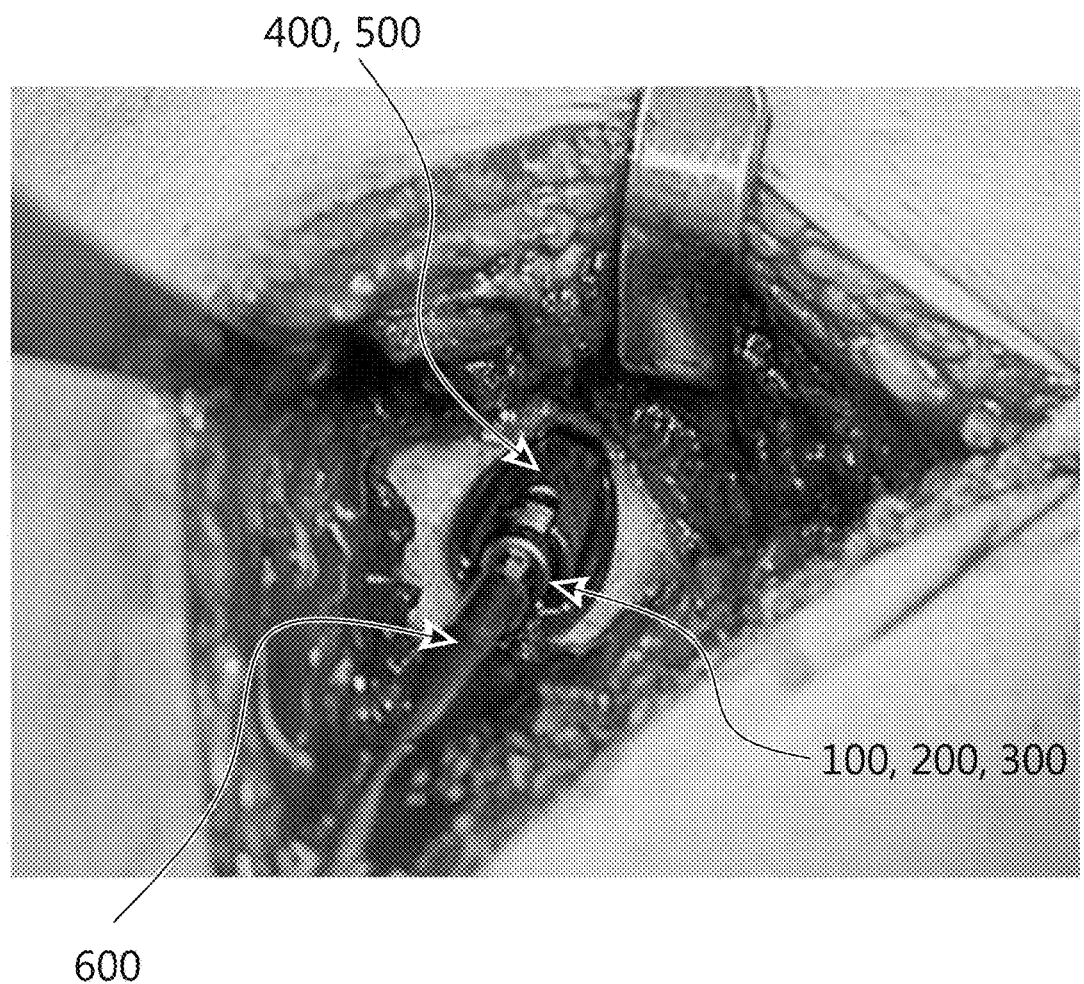
FIG. 9 is an image of an end cap introduction during surgery.

FIG. 9 is an image showing circumstances under which a surgeon may insert an end cap 100, 200, 300 into a trailing end of a bone nail 400, 500. With the end cap at the end of the tool 600, the end cap 100, 200, 300 may be inserted into the trailing end of the bone nail, wherein only a small part of the bone as well as of the bone nail is visible so that the actual orientation of the axis of the bone nail 400, 500 cannot be seen. Furthermore, the insertion of the end cap 100, 200, 300 is difficult as the surrounding soft tissue provides less space to manipulate the tool 600. The invention proposes an end cap an insertion of which is facilitated.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practising the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

LIST OF REFERENCE SIGNS 100 end cap
110 head
120 cone
130 intermediate portion
131 clearance groove
132 shoulder
150 threaded portion
200, 300 end cap
210, 310 head portion
212, 312 inner tool engagement portion
214, 314 rounded edges
216, 316 centre axis
220, 320 conical portion
222, 322 outer surface
224, 324 cone angle
232, 332 chamfer
240, 340 tip
350 sub-portion
360 first circumferential section
362 second circumferential section
364 transition section
270, 370 threads
272, 372 flanks
274, 374 bisecting line
276, 376 pitch
400, 500 bone nail
410, 510 inner threads
512 longitudinal bore
520 through bore
600 tool

The invention claimed is:

1. An end cap for use with an intramedullary nail, comprising:
   a head portion with a tool engagement portion;
   a shaft with a tip; and
   wherein the shaft comprises a conical portion and a sub portion, the conical portion starting from the tip and extending in a direction to the head portion and having a thread with a constant pitch,
   the sub-portion having a first circumferential section without thread and a second circumferential section with thread, wherein the first circumferential section has an outer diameter corresponding to a minor diameter of the thread and extends on at least a third of the circumference of the sub-portion, the second circumferential section having a length extending along a longitudinal axis of the shaft, the first circumferential section extending along at least a portion of the length of the second circumferential section.

2. The end cap of claim 1, wherein the thread comprises a thread profile defining a bisecting line between two adjacent tooth flanks, wherein the bisecting line of the thread profile is perpendicular to the surface of the conical portion.

3. The end cap of claim 1, wherein the thread comprises a thread profile defining a bisecting line between two adjacent tooth flanks, wherein the bisecting line of the thread profile is perpendicular to the longitudinal axis of the end cap.

4. The end cap of claim 1, wherein the conical portion defines an angle of between 8° and 12° to a longitudinal axis of the end cap.

5. The end cap of claim 1,
   wherein the thread has a maximal diameter adjacent to the head portion, which diameter corresponds to a nominal diameter of an inner thread of a bone nail.

6. The end cap of claim 1, wherein the shaft further comprises a cylindrical sub-portion starting from the conical portion and extending in a direction to the head portion, wherein the thread continues with a constant diameter on the cylindrical sub-portion.

7. The end cap of claim 1, wherein the thread has a minimal diameter adjacent to the tip, which minimal diameter corresponds to half of a nominal diameter of an inner thread of a bone nail.

8. The end cap of claim 1, wherein the tip has rounded edges.

9. The end cap of claim 1, wherein a clearance groove is provided on the shaft adjacent the head portion of the end cap.

10. The end cap of claim 9, wherein a chamfer is provided as a transition between the clearance groove and the head portion.

11. The end cap of claim 1, wherein the tool engagement portion is an inner tool engagement portion.

12. An end cap for use with an intramedullary nail, comprising:
    a head portion with a tool engagement portion;
    a shaft with a tip, wherein the shaft comprises a conical portion starting from the tip and extending in a direction to the head portion; and
    wherein a thread with a constant pitch is provided on the conical portion, wherein a first circumferential section without thread and a second circumferential section with thread are formed in a sub-portion of the shaft, wherein the first circumferential section has an outer diameter corresponding to a minor diameter of the thread and extends on at least a third of the circumference of the sub-portion while the remaining circumference of the sub-portion is occupied by the second circumferential section, the circumference extending about a longitudinal axis of the shaft.

13. The end cap of claim 12, wherein the shaft further comprises a cylindrical sub-portion starting from the conical portion and extending in a direction to the head portion, wherein the thread continues with a constant diameter on the cylindrical sub-portion with the maximum diameter of the thread.

14. The end cap of claim 12, wherein the conical portion defines an angle of between 8° and 12° to a longitudinal axis of the end cap.

15. A system comprising:
    an end cap of claim 12;
    a locking screw; and
    a bone nail with an inner thread for receiving the end cap and a transverse bore for receiving the locking screw.

16. The system of claim 15, wherein the end cap is configured to be in contact with an outer surface of the locking screw when the locking screw is inserted in the transverse bore of the bone nail and the end cap is inserted into the inner thread of the bone nail.

17. A system comprising:
an end cap comprising:
- a head portion with a tool engagement portion,
- a shaft with a tip,
- wherein the shaft comprises a conical portion starting from the tip and extending in a direction to the head portion,
- wherein a thread with a constant pitch is provided on the conical portion, and
- wherein the shaft further comprises a cylindrical sub-portion starting from the conical portion and extending in a direction to the head portion, wherein the thread continues with a constant diameter on the cylindrical sub-portion with the maximum diameter of the thread;

a locking screw; and bone nail with an inner thread for receiving the end cap and a transverse bore for receiving the locking screw.

18. The system of claim 17, wherein the conical portion defines an angle of between 8° and 12° to a longitudinal axis of the end cap.

19. The system of claim 17, wherein a clearance groove is provided on the shaft adjacent the head portion of the end cap.

* * * * *